United States Patent [19]
Schmitt et al.

[11] Patent Number: 5,697,970
[45] Date of Patent: Dec. 16, 1997

[54] THINLY WOVEN FLEXIBLE GRAFT

[75] Inventors: Peter J. Schmitt, Garnerville, N.Y.;
Jose F. Nunez, Kearny, N.J.

[73] Assignee: Meadox Medicals, Inc., Oakland, N.J.

[21] Appl. No.: 650,783

[22] Filed: May 20, 1996

Related U.S. Application Data

[63] Continuation of Ser. No. 285,334, Aug. 2, 1994, abandoned.

[51] Int. Cl.$^6$ .................................................. A61F 2/06
[52] U.S. Cl. ........................... 623/1; 623/11; 623/12
[58] Field of Search ........................... 623/1, 8, 9, 11,
623/12, 66; 600/36, 37; 606/191, 194, 198

[56] References Cited

U.S. PATENT DOCUMENTS

| | | | |
|---|---|---|---|
| 3,105,492 | 10/1963 | Jeckel | 623/1 |
| 3,588,920 | 6/1971 | Wesolowki | 623/1 |
| 4,202,349 | 5/1980 | Jones | 623/1 |
| 4,545,082 | 10/1985 | Hood | 623/1 |
| 4,550,447 | 11/1985 | Seiler, Jr. et al. | 623/1 |
| 5,383,927 | 1/1995 | De Goicoechea et al. | 623/12 |
| 5,476,506 | 12/1995 | Lunn | 623/12 |

FOREIGN PATENT DOCUMENTS

| | | | |
|---|---|---|---|
| 2913510 | 10/1979 | Germany | 623/1 |
| 8303347 | 10/1983 | WIPO | 623/1 |
| 8806026 | 9/1991 | WIPO | 623/1 |

*Primary Examiner*—John G. Weiss
*Assistant Examiner*—Francis K. Cuddihy
*Attorney, Agent, or Firm*—Hoffmann & Baron, LLP

[57] ABSTRACT

A thinly woven textile prosthetic implant such as a vascular graft may be implanted by catheter implantation. The implant includes an elongate tubular body formed of a woven fabric having a fabric thickness no greater than about 0.16 mm. The tubular body includes a series of longitudinally spaced wave-like generally uniform crimps along the length thereof. The crimps are disposed at a fine pitch along the length of the tubular body. The amplitude of the crimps is relatively small thus reducing the formation of thrombus and plaque on the inside of the implant.

16 Claims, 2 Drawing Sheets

THINLY WOVEN FLEXIBLE GRAFT

This is a continuation of application(s) Ser. No. 08/285,334 filed on Aug. 2, 1994, abandoned May 21, 1996.

FIELD OF THE INVENTION

The present invention relates generally to synthetic tubular prostheses and more particularly the present invention relates to a flexible vascular graft formed of thinly woven textile material.

BACKGROUND OF THE INVENTION

Textile grafts are widely used to replace or repair damaged or diseased vessels of the body. Textile vascular grafts may be implanted in the vascular system for the repair of arteries and veins. Traditionally, graft implantation is conducted in a surgical procedure requiring the body to be opened adjacent to the implantation site. Improvements in medical procedures now additionally permit graft implantation to be done in a less invasive manner. Vascular endoscopic surgery permits certain grafts to be implanted with a hollow catheter delivery system. The catheter enters the vessel either percutaneously or through a small incision. The catheter delivery system passes the graft through the lumen of the blood vessel for deployment at the desired location. In order to minimize trauma at the site of insertion of the catheter, it is desirable to employ the smallest diameter catheter possible. Accordingly, a graft which is to be implanted by the catheter delivery system would also have to be as thin as possible so that it can be radially compressed and packed inside the lumen of a hollow catheter for deployment in the blood vessel. As the size of the graft dictates the size of the catheter employed, providing a thin graft allows use of a small diameter catheter and therefore results in less trauma during implantation.

Traditional grafts currently available, having a wall thickness of 0.25 to 0.75 mm, are designed for surgical implantation and would not lend themselves to successful catheter delivery. Also, since catheter delivery is typically done under a fluoroscope or other similar x-ray type viewing mechanism, the movement of traditional textile vascular grafts during deployment cannot be fluoroscopically viewed. Further, as with traditional surgically implanted grafts, catheter implanted grafts must be longitudinally flexible to conform to the shape of the vessel which it is repairing. Also, such grafts should be capable of a certain degree of longitudinal expansion to conform to the length of the blood vessel which is to be replaced. Finally, the graft, once implanted by the catheter delivery system, must readily return to its open tubular shape and maintain that shape during use. This is particularly important where the graft is implanted by a catheter as the graft must be tightly compressed and packed so as to fit within the hollow lumen of the catheter.

In order to maintain the desired flexibility, longitudinal expansion and a certain degree of radial structural integrity, it is known to provide pleated, wave-like corrugations or crimps along the length of a textile vascular graft. These crimps provide flexibility to the graft and the ability for the graft to longitudinally expand in a spring-like manner.

An example of a traditional surgically implanted graft having wave-like crimps or corrugations to provide flexibility, stretch and radially support is shown in U.S. Pat. No. 3,142,067. As can be seen in the '067 patent, these wave-like crimps or corrugations have a relatively large amplitude so as to impart the desired degree of flexibility, stretch and structural integrity to the graft. Such large crimps in the wall of the graft presents an irregular profile of the graft wall with a relatively large difference between the major and minor diameter thereof. This area is susceptible to thrombus and plaque formation and build-up which is undesirable in a vascular graft.

It is therefore desirable to provide an improved thinly woven textile graft which exhibits sufficient spring-like elasticity and flexibility and which may be compressed in a manner which permits catheter implantation into a blood vessel.

SUMMARY OF THE INVENTION

It is an object of the present invention to provide a thinly woven textile prosthetic implant capable of being catheter implanted into a body lumen.

It is a further object of the present invention to provide a thinly woven textile graft having a fabric thickness not exceeding about 0.16 mm and having a pattern of fine cramps therealong.

It is a still further object of the present invention to provide a thinly woven textile graft having a pattern of finely spaced wave-like crimps therealong wherein the peak-to-peak amplitude of the wave-like crimps does not exceed 0.5 mm.

In the efficient attainment of these and other objects, the present invention provides a woven textile prosthetic implant including an elongate tubular body formed of a woven fabric having a fabric thickness which is no greater than about 0.16 mm. The tubular body includes a series of longitudinally spaced wave-like generally uniform crimps along the length thereof. The crimps have a crimp frequency of no less than about 6 crimps per centimeter of body length.

As further described by way of the preferred embodiment herein, the wave-like generally uniform crimps include a peak-to-peak amplitude which is no greater than about 0.5 mm. This reduces the area in which thrombus formation may take place.

Additionally, the present invention specifically provides an intraluminally implantable graft having a wall thickness sufficiently thin such that the graft may be radially compressed for insertion into a delivery catheter for catheter implantation.

DETAILED DESCRIPTION OF THE PREFERRED EMBODIMENTS

The present invention provides an improved textile prosthetic implant. Specifically the preferred embodiment of the present invention is directed towards an implantable graft which is used to replace a damaged section of a body vessel such as a blood vessel. However, the present invention need not be limited thereto. A prosthetic implant in accordance with the present invention may be used intraluminally to support any diseased or otherwise damaged body vessel.

Figure 1:
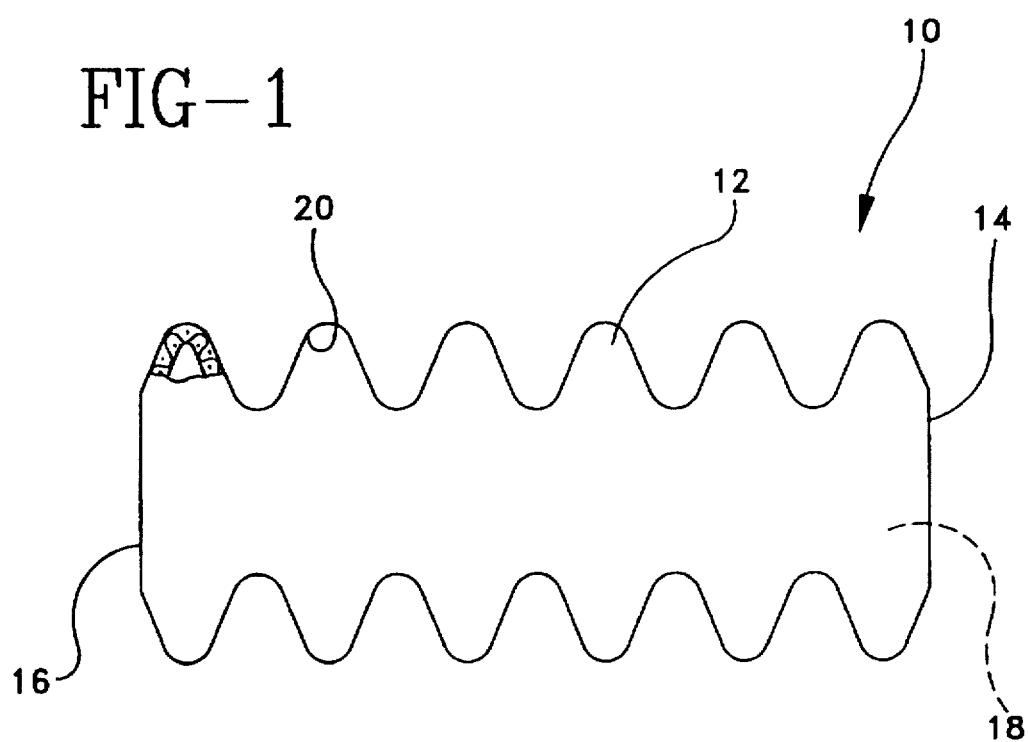
FIG. 1 shows schematically, in partial section, a conventionally formed prosthetic graft.

Referring to FIG. 1, a conventional vascular graft 10 is shown. Graft 10 is a textile product formed of a woven or knitted synthetic fabric in a manner which is well known in the graft art. Graft 10 includes a generally tubular body 12 having opposed ends 14 and 16 which define therebetween an open lumen 18 which permits passage of blood once the graft 10 is implanted in the blood vessel. As graft 10 is designed to repair or replace a damaged or missing blood vessel, typically in a surgical procedure, the graft must be suitably pliable to adapt to the configuration of the vessel into which it is being implanted and also must be flexible enough to be handled and manipulated by the surgeon. As important, once the graft 10 is implanted, the graft must maintain a tubular configuration so that lumen 18 remains open allowing the passage of blood.

In order to enhance the pliability, ease of handling and structural stability of the tube, it has been known to provide tubular graft 10 with a series of wave-like crimps 20 along the body thereof. Crimps 20 follow a generally sinusoidal wave-like pattern continuously along the length of graft 10. Crimps 20 may be imparted to graft 10 in one of a number of well-known techniques. For instance, the uncrimped tubular graft may be compressed over a mandrel and then by an application of heat, the crimp pattern will take a set. Other techniques such as disposing graft 10 over a screw-threaded mandrel and heating the mandrel, may also impart a desired crimp-like pattern to the graft. Regardless of the technique used to form the wave-like crimps, the number and size of crimps on any particular graft is limited by the fabric or wall thickness of the graft. Where the wall thickness of the graft is relatively thick, say greater than 0.20 mm, successive crimps cannot be closely spaced. That is, the graft cannot have finely pitched crimps. Thus, it can be appreciated that the relative thickness of the fabric prevents the waves from being closely compacted. Accordingly in order to establish the longitudinal flexibility needed, as well as to impart sufficient tubular integrity, it is necessary to provide wave-like crimps having a relatively large amplitude. The amplitude of the wave, which is dictated by the thickness of the fabric, permits the graft to be longitudinally stretched so as to conform to the portion of the blood vessel which must be replaced or repaired. Further, such large amplitude crimps permit the graft to be easily flexed to permit ease of implantation and also provide a certain degree of structural stability to maintain the graft in an open tubular configuration.

However, when employing the graft as a vascular graft, the large amplitudes of the crimps have a tendency to promote the formation of thrombus and plaque build-up between the crimps which may be detrimental to the long-term patency of the graft. Further, the relatively large amplitude crimps provide a significantly more irregular profile of the graft wall which can undesirably increase the amount of turbulence created within the vessel.

Heretofore attempts to provide a graft with finer pitched crimps of lower amplitude have been found to be unacceptable for usage. Thick wall grafts having finer crimps and/or crimps of lower amplitude do not exhibit a sufficient pliancy, spring-like elasticity and structural integrity to be suitable for implantation.

Figure 2:
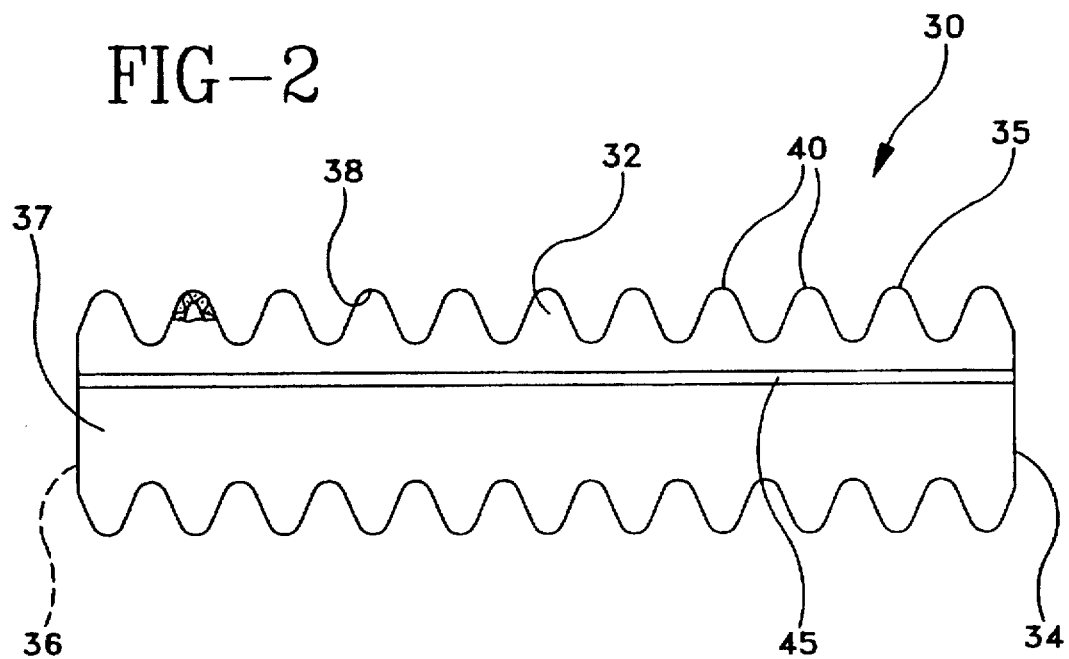
FIG. 2 shows schematically, in partial section, a prosthetic graft formed in accordance with the present invention.

Referring now to FIG. 2, the graft of the present invention may be described. Graft 30 is an elongate generally tubular member formed of woven synthetic fibers such as polyester. However it may be appreciated that other materials, as well as other forming techniques such as knitting may also be employed. Graft 30 includes a tubular body 32 having opposed ends 34 and 36 which define therebetween an open lumen 37. Graft 30 defines a generally tubular fabric wall 35 having a fabric thickness not exceeding about 0.16 mm.

An example of a graft formed in accordance with the present invention may be formed from a plain weave tubular fabric having a warp yarn of 50 denier, 48 filament flat polyester and weft yarn of 50 denier, 48 filament flat polyester. The ends per inch would be 188 per layer while the picks per inch would be 88 per layer. The fabric so formed would have a wall thickness of approximately 0.12 mm. After weaving into a tubular graft, the graft would be scoured to remove dirt, oil and other processing agents. The material may be then heat set to stabilize the graft. Heat setting can be accomplished in one of many conventionally known techniques such as heating in a steam autoclave or a conventional oven. The tubular fabric can also be heat set on smooth mandrels to precisely set the diameter and to remove any creases or wrinkles. As above described, the grafts may then be crimped to impart longitudinal compliance and radial support.

As the grafts of the present invention have a fabric wall thickness which is much thinner than grafts presently conventionally available, a finer crimp pattern may be imparted to graft 30 of the present invention. Crimp pattern 40 shown in FIG. 2 includes a series of wave-like crimps 38 therealong. Crimps 38 may be imparted on a finer pitch as the relatively thin fabric would not impede such fine pinch crimping.

It has been found that the maximum number of crimps that can be imparted to a tubular graft follows the equation:

$$C=[2(t+10)]^{-1}$$

where C is the number of crimps per centimeter of length of the tube and t is the fabric or wall thickness of the graft.

Thus, a graft having a maximum fabric or wall thickness of 0.16 mm could be crimped to a pitch of about 33 crimps per centimeter. By permitting such a fine crimp pattern along the length of tubular graft 30, the amplitude of the crimps can be reduced without significantly reducing the longitudinal flexibility or structural stability of the graft. It has been found that forming a graft in accordance with the present invention, the amplitude, measured peak-to-peak, of the wave-like crimp pattern can be reduced to no greater than 0.5 mm. A crimp pattern having such a small amplitude greatly reduces risk of thrombus or plaque formation on the interior of the graft.

The thinly woven graft of the present invention may be radially compressed for insertion within the lumen of the catheter (not shown) for catheter implantation within a body vessel. The thin construction of the graft of the present invention permits such catheter implantation. The above described example permits use of a small diameter endoluminal catheter which tends to reduce trauma at the insertion site. In the preferred example describe above, catheters such as an 8 cm long balloon, PE-MT balloon angioplasty catheter manufactured by Meditech-Boston Scientific, Inc. or a 10 mm diameter by 4 cm long OLBERT® balloon catheter manufactured by Meadox Surgimed A/S may be employed for introducing and implanting graft 30.

Once deployed, the graft 30 must maintain its longitudinal flexibility as well as return to its tubular open lumen configuration. The particular pattern of crimps employed with the present invention permits such longitudinal flexibility and structural integrity without increasing the graft thickness as measured both by fabric wall thickness and as measured between the peak-to-peak amplitude of the wave-like pattern of crimps.

In addition, as graft 30 is designed to be catheter implanted it is generally desirable to provide means for viewing the implanted graft fluoroscopically. Graft 30 may include a radiopaque guideline or marker. As shown in FIG. 2, marker 45 may extend the length of graft 30. Other patterns for marker 45 may also be employed. Radiopaque marker 45 assists the surgeon to visualize the graft both during and after implantation. The marker 45 would help show the surgeon that the graft is properly positioned. Also, it will indicate whether the graft has dilated or collapsed after implantation. Further, during endoscopic implantation, marker 45 may be used to assist in the proper positioning of the graft.

As is well known, radiopaque guidelines or markers may be formed from metallic fibers such as stainless steel or titanium. Also, one or more polymeric fibers may be coated or filled with radiopaque particles.

Figure 3:
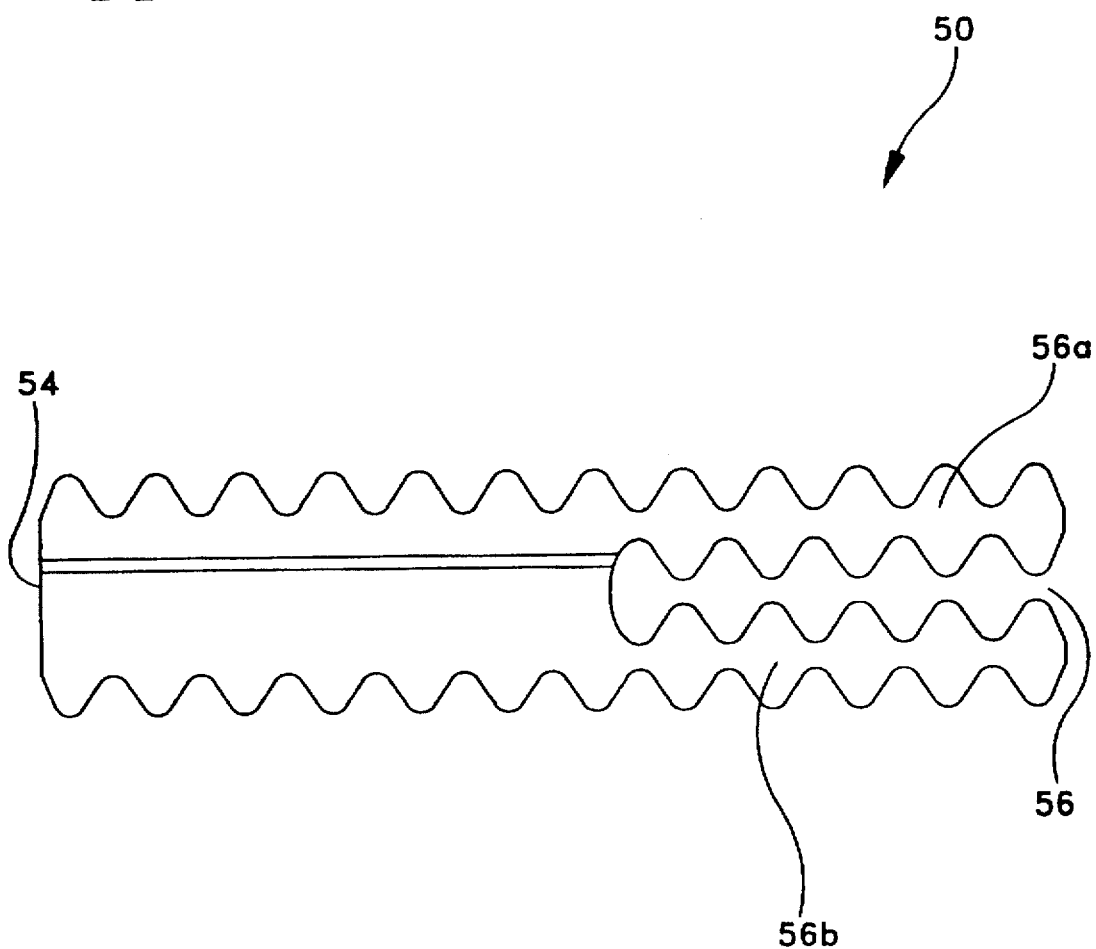
FIG. 3 shows schematically, in partial section, the present invention embodied in a bifurcated design.

The present invention is not limited to the graft shape show in FIG. 2, other graft configurations are within the contemplation thereof. For example, referring to FIG. 3, a bifurcated graft 50, may also be formed in accordance with the present invention. Graft 50 is an elongate generally tubular member having a first end 54 having a single lumen extending therefrom. An opposed end 56 is bifurcated into a pair of smaller tubular members 56a and 56b. A graft of this type may be used to repair and replace a main vessel and branch vessels. In accordance with the present invention graft 50 is crimped in a manner described above to impart longitudinal flexibility, structural integrity and spring-like compliance.

Various changes to the foregoing described and shown structures would now be evident to those skilled in the art. Accordingly, the particularly disclosed scope of the invention is set forth in the following claims.

What is claimed is:

1. A woven textile prosthetic implant comprising:

an elongate tubular body formed of a fabric wall having a fabric wall thickness no greater than about 0.16 mm, said tubular body having longitudinally spaced wave-like, generally uniform crimps along the length thereof, said crimps extending on both sides of said tubular body and having a crimp frequency of no less than about 6 crimps per centimeter.

2. A woven textile prosthetic implant of claim 1 wherein said tubular body includes an x-ray detectable, radiopaque yarn therein.

3. A woven textile prosthetic implant of claim 2 wherein said radiopaque yarn extends longitudinally along the length of the tubular body.

4. A woven textile prosthetic implant of claim 1 wherein said wave-like crimps have a peak-to-peak amplitude of no greater than about 0.5 mm.

5. A woven textile prosthetic implant of claim 1 wherein said body has a fabric thickness of about 0.12 mm and a maximum crimp frequency of about 42 crimps per cm.

6. A woven textile graft comprising:

an elongate tubular graft body having a wall, said wall having a thickness of no greater than about 0.16 mm and defining a pattern of wave-like crimps extending along both sides of said tubular body, the number of crimps, C, per centimeter of body length being defined by an equation:

$$C=[2(t \rightarrow 10)]^{-1};$$

wherein t equals the body wall thickness in mm.

7. A woven textile graft of claim 6 wherein said wave-like crimps define a peak-to-peak amplitude of no greater than about 0.5 mm.

8. A woven textile graft of claim 7 wherein said tubular body includes a radiopaque marker therein.

9. A woven textile graft of claim 8 wherein said marker extends the length of said tubular body.

10. A woven textile graft of claim 1 wherein said tubular body is bifurcated.

11. A woven textile intraluminally implantable graft comprising:

an elongate tubular graft body having a wall, said wall having a thickness of dimension such that the graft body is capable of being radially compressed for insertion into a delivery catheter;

said tubular graft body having a plurality of longitudinally spaced wave-like crimps along the length thereof on both sides of said tubular body, said wave-like crimps defining a crimp frequency of no less than 8 crimps per cm.

12. A woven textile graft of claim 11 wherein said wall thickness is no greater than about 0.16 mm.

13. A woven textile graft of claim 12 wherein said crimps have a generally uniform peak-to-peak amplitude not exceeding about 0.5 mm.

14. A woven textile graft of claim 13 wherein said tubular body includes a radiopaque marker therein.

15. A woven textile graft of claim 11 wherein said tubular body may be compressed for insertion into an endoluminal catheter.

16. A woven textile graft of claim 11 wherein said tubular graft body is bifurcated.

* * * * *

UNITED STATES PATENT AND TRADEMARK OFFICE
CERTIFICATE OF CORRECTION

PATENT NO. : 5,697,970
DATED : December 16, 1997
INVENTOR(S) : Schmitt et al.

It is certified that error appears in the above-indentified patent and that said Letters Patent is hereby corrected as shown below:

Column 2, Line 21,   now reads, "cramps",
   should read --crimps--,

IN THE CLAIMS:

Claim 6, Line 9,   now reads "$C=[2(t\rightarrow 10)]^{-1}$",
   should read --$C=[2(t\div 10)]^{-1}$--.

Signed and Sealed this

Twenty-first Day of April, 1998

Attest:

BRUCE LEHMAN

Attesting Officer   Commissioner of Patents and Trademarks